United States Patent [19]

Hovey et al.

[11] Patent Number: 4,639,539

[45] Date of Patent: Jan. 27, 1987

[54] DIMERIZATION PROCESS IMPROVEMENTS

[75] Inventors: Leonard L. Hovey; Marion J. Mathews, III; P. Robert Peoples, all of Pensacola, Fla.

[73] Assignee: Monsanto Company, St. Louis, Mo.

[21] Appl. No.: 804,013

[22] Filed: Dec. 3, 1985

Related U.S. Application Data

[63] Continuation-in-part of Ser. No. 686,109, Dec. 24, 1984, abandoned, and a continuation-in-part of Ser. No. 664,625, Oct. 25, 1984, abandoned.

[51] Int. Cl.$^4$ .......................................... C07C 121/30
[52] U.S. Cl. .................................................. 558/363
[58] Field of Search ................ 260/465.8 D, 465.8 R; 558/363

[56] References Cited

U.S. PATENT DOCUMENTS

| | | | |
|---|---|---|---|
| 3,375,237 | 3/1968 | Bazier | 260/465.8 D UX |
| 4,089,890 | 5/1978 | Jennings et al. | 260/465.8 D |
| 4,100,186 | 7/1978 | Wright | 260/465.8 D |
| 4,102,915 | 7/1978 | Jennings et al. | 260/465.8 D |
| 4,126,632 | 11/1978 | Hogan et al. | 260/465.8 D |
| 4,138,428 | 2/1979 | Jennings et al. | 260/465.8 D |
| 4,238,422 | 12/1980 | Cozens et al. | 260/465.8 D X |
| 4,263,224 | 4/1981 | Jennings et al. | 260/465.8 D |
| 4,316,857 | 2/1982 | Gilbert | 260/465.8 D |

OTHER PUBLICATIONS

Takashina et al.; J.A.C.S., 84, (1962), pp. 489–491.
McClure; J. Org. Chem., 35, (1970), pp. 3045–3048.
Dietsche; Tetrahedron Letters, (1966), pp. 6347–6351.

*Primary Examiner*—Joseph Paul Brust
*Attorney, Agent, or Firm*—Thomas N. Wallin

[57] ABSTRACT

Acrylonitrile is catalytically dimerized in the presence of an organic phosphorus (III) catalyst, an inert hydrocarbon reaction solvent and a non-interfering proton-donating solvent; and the dimerized product separated from the catalyst by extraction. In the extraction the dimerized product is preferably dissolved in an extraction solvent and removed from the catalyst phase preparation. In the instant invention, the extraction solvent is an amide, preferably formamide. The extraction solvent and proton-donating solvent may be identical.

4 Claims, 1 Drawing Figure

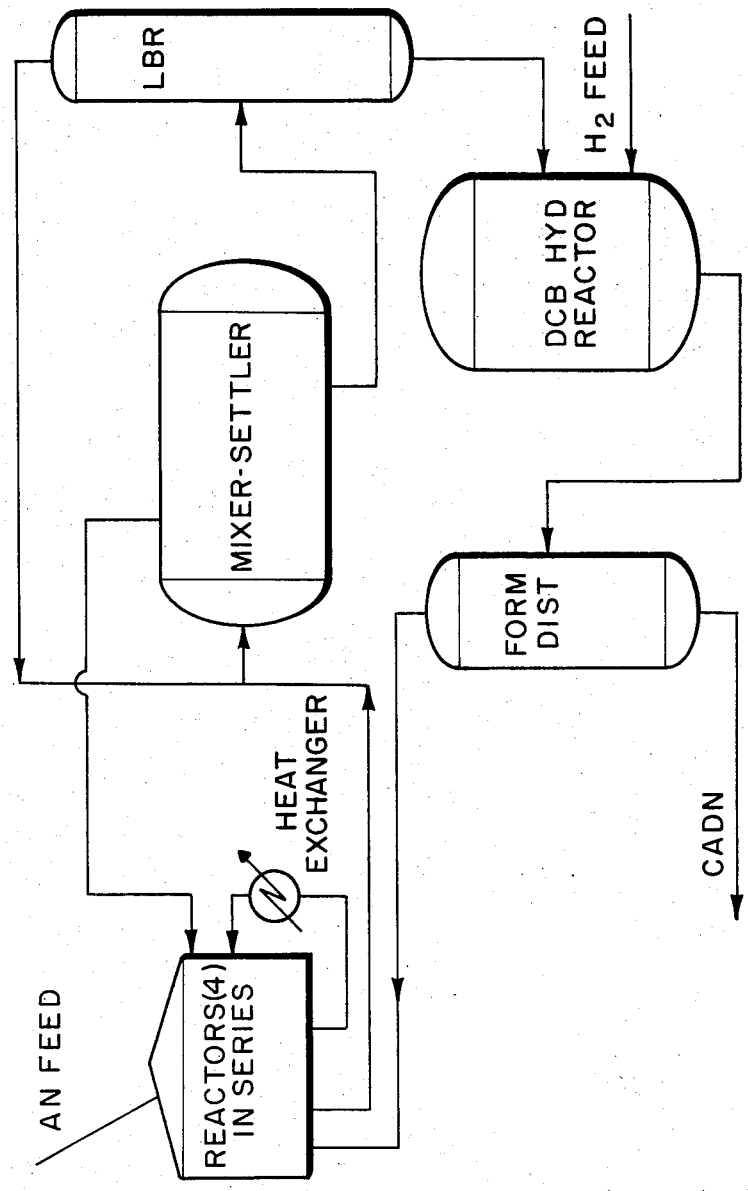

DIMERIZATION PROCESS IMPROVEMENTS

BACKGROUND OF THE INVENTION

This application is a continuation-in-part of U.S. patent application Ser. No. 686,109 filed Dec. 24, 1984 and U.S. patent application Ser. No. 664,625 filed Oct. 25, 1984 both of said applications being now abandoned.

FIELD OF THE INVENTION

This invention relates to dimerization process improvements and especially to improvements in a process for the dimerization of acrylonitrile to linear $C_6$ dinitriles.

BACKGROUND OF THE INVENTION

Processes for the dimerization of acrylonitrile to essentially straight-chain $C_6$ dimers are well known in the prior art as illustrated by U.S. Pat. Nos. 4,102,915, 4,126,632 and 4,138,428. Generally speaking, these patents describe processes in which acrylonitrile is contacted with an organic phosphorus (III) compound which has at least one hydrocarbyl and at least one alkoxy or cycloalkoxy group attached to the phosphorus atom or atoms, the acrylonitrile being dissolved in an organic solvent capable of donating protons.

According to most of these teachings, the phosphorus (III) compound has any one of the following formulae:

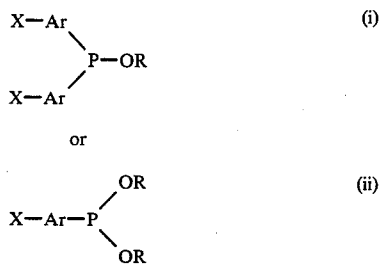

where Ar is an aromatic nucleus, e.g. phenyl or naphthyl, and where groups X, which may be the same or different, are hydrogen or electron donating substituents of the aromatic nucleus which give rise to a negative Hammett $\sigma$ constant; and R represents an alkyl or cycloalkyl group. Substituents X may be in the para or meta positions; but are preferably para. In the case of compounds of formula (i) above, substituents X may be para in one Ar group but meta in the other.

It will be appreciated that the phosphorus (III) compounds defined above are either phosphinites or phosphonites.

A discussion on Hammett $\sigma$ constants and a table showing values for most common substituents is to be found in an article by Clark and Perrin in Quarterly Reviews, Vol 18, 1964 pp 295-320.

Examples of suitable substituents X include alkoxy groups, e.g. methoxy, ethoxy, i-propoxy and t-butoxy; alkyl groups, e.g. methyl, ethyl and propyl; and alkyl amino groups, e.g. dimethylamino and diethylamino. The alkoxy, alkyl and alkylamino groups preferably contain from 1 to 8 carbon atoms. It is essential that group X should be one which does not react adversely with the components of the reaction system.

Suitable R groups include alkyl groups such as methyl, ethyl, isopropyl, neopentyl, 2-ethylhexyl; and cycloalkyl groups such as cyclohexyl. It is noted that bulky groups R, for example isopropyl, may give rise to increased catalyst lifetime.

In accordance with these teachings, the presence of an organic solvent is essential to the process because in the absence of such a solvent rapid polymerization occurs. These solvents are said to be "proton-donating solvents" which are substantially unreactive in respect of addition to, or reaction with, the unsaturated linkage of the acrylonitrile or the products of acrylonitrile dimerization. It is taught that the solvent must not react with the phosphorus compounds or catalytic intermediates to form inactive phosphorus species at such a rate as to seriously impair the dimerization reaction.

While the proton donating solvents were not limited to alcohols, alcohols were strongly preferred because they did not react adversely with the phosphorus compound or any intermediates the phosphorus compound may form with the acrylonitrile. Tertiary and secondary alcohols were preferred as for example, t-butylalcohol, 2-butanol and isopropylalcohol.

In order to reduce the amount of hexamer and/or other oligomers and polymers (referred to as polymeric by-products) which were co-produced with the desired dimeric products, it was considered desirable to add a non-hydroxylic co-solvent to the reaction mixture.

These non-hydroxylic organic solvents included hydrocarbons such as hexane, cyclohexane, benzene, toluene, and petroleum ethers; ethers, such as tetrahydrofuran, diethyl ether and diisopropyl ether; nitriles, such as acetonitrile, propionitrile and fluorobenzenes. The hydrocarbon co-solvents were generally preferred.

In accordance with prior art processes, the desired products were readily separated from the reaction mixtures, for example, by fractional distillation or solvent extraction.

SUMMARY OF THE INVENTION

In accordance with the present invention acrylonitrile is catalytically dimerized in the presence of an organic phosphorus (III) catalyst, a non-interfering proton donating solvent and preferably an inert hydrocarbon reaction solvent, and the dimerized product is thereafter separated from the catalyst by extraction in which extraction the dimerized product is dissolved in the extraction solvent which dissolves the catalyst and reaction solvent minimally, and most of the dimerized product is removed from the catalyst while in such dissolved state, preferably by phase separation.

In accordance with the present invention, the extraction solvent is preferably an amide of the empirical formula

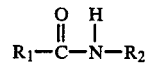

where $R_1$ and $R_2$ individually have 0-6 carbon atoms and are individually selected from the group consisting of hydrogen, alkyl, cycloalkyl and aryl, which may also be used as the proton-donating solvent.

In the detailed description, reference will be made to the drawing in which the FIGURE is a process flow diagram illustrating the practice of this invention.

DETAILED DESCRIPTION OF THE INVENTION

As indicated above, acrylonitrile is catalytically dimerized in the presence of an organic phosphorus (III) catalyst, a non-interfering proton donating solvent and preferably an inert hydrocarbon reaction solvent, and the dimerized product is thereafter separated from the catalyst by extraction in which extraction the dimerized product is dissolved in the extraction solvent which dissolves the catalyst and reaction solvent minimally, and most of the dimerized product is removed from the catalyst while in such dissolved state, preferably by phase separation. As indicated above in accordance with the present invention, the extraction solvent is an amide of the empirical formula

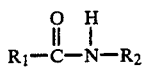

where $R_1$ and $R_2$ individually have 0-6 carbon atoms and are individually selected from the group consisting of hydrogen, alkyl, cycloalkyl and aryl, which may also be used as the proton-donating solvent.

The proton-donating solvent may be any of the tertiary or secondary alcohols such as t-butylalcohol, 2-butanol or isopropylalcohol which do not react adversely with the phosphorus catalyst, all as described in the prior art listed above. The proton-donating solvent may also be a specific amide such as described above as the extraction solvent. While it is not necessary, the same solvent may be used as proton-donating solvent and extraction solvent. Much of the following is written in contemplation of such identity of proton-donating and extraction solvents.

Aside from this critical difference in solvent usage, the teachings of the prior art are applicable to the process. For example, it is desirable that the reaction be conducted in the substantial absence of water. It is believed that water reacts with the catalyst in the presence of acrylonitrile and/or dimeric products to give non-catalytic addition compounds. Thus the acrylonitrile, the proton-donating solvent and the reaction co-solvent must be dried before use or the catalyst life may be reduced to a commercially unacceptable level. Acrylonitrile, which commonly contains as much as 4000 ppm of water, even after distillation, should be rigorously dried. Phenolic stabilizers, such as hydroquinone and its monoethyl ether, p-methoxyphenol, which are present in acrylonitrile as ordinarily commercially supplied, should be removed, as for example, by treatment with activated alumina.

Any suitable drying technique may be used, provided that the final water level is sufficiently low. For example, acrylonitrile and hydroxylic solvents may be dried by being contacted with calcium hydride or a 3A or 4A molecular sieve.

Generally the concentration of acrylonitrile in the solvent or solvent mixture should range from 5 to 75% by volume. The concentration of acrylonitrile is kept as high as possible in order to optimize throughput and thus concentrations in the range of 10 to 50% by volume are generally preferred.

The concentration of the phosphorus compound in the reactant mixture may be varied over a wide range, for example, from 0.005, to 15% by volume, calculated on the volume of liquid reactants; but preferably the concentration is in the range 1% to 5% by volume.

When present, the proportion of co-solvent in the reaction mixture may be varied over wide limits. In general the ratio of proton-donating solvent to co-solvent is in the range 1/200 to 40/1; but ratios at the lower end of the range are generally preferred. However, the final choice of solvent/co-solvent ratio will depend on how it is desired to run the process and the catalyst compound used. For example, ratios in the range 1/150 to 1/10 may give rise to enhanced catalyst lifetime and increased selectivity to linear dimer, when compared with an equivalent reaction where the ratio is 1/1.

Changes in the ratio of proton-donating solvent/co-solvent are generally reflected by changes in the amount of polymers formed and changes in the reaction rate. These changes in reaction parameters are often dependent upon the actual catalyst and solvent system chosen.

The ratio of linear to branched dimers is also dependent on the solvent/co-solvent ratio in some instances. It is sometimes found that, as the proportion of proton-donating solvent decreases, the proportion of linear dimer increases, and vice-versa.

The reaction temperature is commonly in the range 0° to 180° C.; but it may be preferred to keep the range temperature below 75° C. to minimize undesirable side reactions. It is noted that the reaction will proceed below 0° C., maintaining selectivity, but at a reduced rate. In fact, in some cases improved selectivity may be obtained at lower temperatures.

The reaction may be carried out batchwise or continuously. In the latter case, it may be convenient to support the catalyst compound or to use a polymeric trivalent phosphorus compound to enable the reaction to be carried out in the liquid phase using a heterogeneous catalyst.

The dimeric products of our invention are predominantly linear $C_6$ dinitriles, especially the 1,4-dicyanobutenes. Selectivities >90 wt % (calculated on total dimeric product) may be readily obtained.

Testing formamide as both extraction and proton-donating solvent, a typical composition at start of reaction:

Acrylonitrile: 20% (by weight)
Formamide: 4%
Toluene: 72%
Catalyst: 4%
Temperature: 30° C.
Reaction Time: 10 hours The system may or may not begin as a two-phase reaction. The system may or may not be two phases at the end of the reaction. Phase behavior is dependent on composition, temperature and conversion and does not impact process feasibility. The attached table exemplifies typical formamide levels and results.

Permissible variations in content of essential elements of the invention:

Acrylonitrile (AN): 1–50% (by weight)
Toluene (TOL): 30–90%
Formamide (FORM): 0.01–20%
Isopropyl alcohol: 0–20%
Catalyst (CAT): 1–20%

Referring now to the FIGURE, the reactor, one or several in either series or parallel flow, contains acrylonitrile, toluene, catalyst, and formamide which will separate into two phases upon settling. The light phase from the reactor is pumped through a heat exchanger, to remove the heat of reaction, back to the reactor.

Formamide, either fresh, recycle or heavy phase from one of the other reactors, is mixed with the light phase and the two phases allowed to separate in the reactor, or a separate setting vessel. The dicyanobutene (DCB) product concentrates in the formamide layer and is pumped forward to the next stage reactor or product separator. The formamide layer, rich in DCB product leaving the reactor, is contacted with catalyst free recycle and makeup toluene and acrylonitrile to remove residual catalyst from the formamide layer. The light phase is returned to the reactor and the heavy phase is pumped to a low boiler removal column. The overhead from the low boiler removal column is mixed with makeup toluene and acrylonitrile and used for removal of the residual catalyst from the formamide layer from the last stage or product separator. The tails from the low boiler removal column are sent to a hydrogenation step to convert DCB to adiponitrile. The formamide is separated from the adiponitrile by distillation with the formamide being recycled to the first reactor and the adiponitrile is taken forward as product.

EXAMPLES 1–24
(showing use of formamide as proton-donating solvent and extraction solvent)

A 50 ml septum capped vial, dried and purged with nitrogen was charged with the following components in the proportions given in Examples 1–24.

Toluene (TOL)
Acrylonitrile (AN)
Formamide (FORM)
Isopropyl Alcohol (IPA)
Catalyst: Isopropyl Diphenyl-Phosphinite (PACAT)

TABLE 1
Effect of Formamide on Dimer Synthesis

| | EXAMPLE NUMBER | | | | | | | | | |
|---|---|---|---|---|---|---|---|---|---|---|
| | 1 | 2 | 3 | 4 | 5 | 6 | 7 | 8 | 9 | 10 |
| FEED COMP, % | | | | | | | | | | |
| FORMAMIDE | 5.2 | 10.1 | 2.6 | 2.5 | 2.5 | 1.0 | 0.5 | 1.0 | 1.0 | 1.0 |
| AN | 19.9 | 19.6 | 19.7 | 19.6 | 19.2 | 19.6 | 19.6 | 20.3 | 20.3 | 19.2 |
| IPA | 6.4 | 6.4 | 6.3 | 3.8 | 6.2 | 5.3 | 5.8 | 1.4 | 2.8 | 4.0 |
| TOL | 64.4 | 59.8 | 67.4 | 70.1 | 68.1 | 70.0 | 70.1 | 73.2 | 71.9 | 71.1 |
| CAT | 4.1 | 4.1 | 4.1 | 4.0 | 4.0 | 4.0 | 4.0 | 4.1 | 4.1 | 4.1 |
| TYPE CAT | ←PACAT→ | | | | | | | | | |
| REACTOR TEMP, °C. | ←30→ | | | | | | | | | |
| RESIDENCE TIME, hr | ←10.5→ | | | | | | | | | |
| PRODUCT COMP, % | | | | | | | | | | |
| AN | 3.2 | 3.7 | 4.7 | 6.2 | 4.8 | 6.9 | 7.6 | 10.7 | 8.8 | 7.6 |
| CDCB (cis-dicyanobutene-1) | 5.62 | 5.26 | 5.62 | 6.61 | 5.57 | 6.43 | 6.26 | 6.42 | 6.80 | 6.60 |
| TDCB (trans-dicyanobutene-1) | 3.67 | 3.35 | 3.33 | 3.19 | 3.23 | 3.25 | 3.38 | 2.15 | 2.78 | 2.91 |
| MEGN (methyleneglutaronitrile) | 0.47 | 0.45 | 0.41 | 0.40 | 0.40 | 0.40 | 0.38 | 0.35 | 0.38 | 0.38 |
| H.B. (high boilers) | 3.22 | 2.76 | 2.74 | 1.56 | 2.47 | 1.79 | 0.92 | 0.46 | 0.80 | 0.93 |
| SOLIDS | 2.43 | 1.86 | 2.94 | 1.64 | 2.76 | 1.47 | 1.07 | 0.10 | 0.81 | 0.92 |
| PROD. SELEC., % | | | | | | | | | | |
| DCB | 60.3 | 62.9 | 59.5 | 73.1 | 61.0 | 76.0 | 80.3 | 90.4 | 82.8 | 81.0 |
| MEGN | 3.0 | 3.3 | 2.7 | 3.0 | 2.8 | 3.1 | 3.2 | 3.7 | 3.3 | 3.2 |
| H.B. | 20.9 | 20.2 | 18.2 | 11.6 | 17.1 | 9.3 | 7.6 | 4.9 | 6.9 | 7.9 |
| SOLIDS | 15.8 | 13.6 | 19.6 | 12.3 | 19.1 | 11.6 | 8.9 | 1.0 | 7.0 | 7.9 |

TABLE 2
Effect of Formamide on DIMER Synthesis

| | EXAMPLE | | | | |
|---|---|---|---|---|---|
| | 11 | 12 | 13 | 14 | 15 |
| FEED COMP, % | | | | | |
| FORMAMIDE | 0.5 | 0.5 | 0.5 | 0.5 | 2.1 |
| AN | 20.8 | 20.7 | 21.0 | 21.3 | 20.7 |
| IPA | 1.5 | 2.9 | 0.75 | 0 | 0 |
| TOL | 73.1 | 71.8 | 73.6 | 74.1 | 73.1 |
| CAT | 4.1 | 4.1 | 4.1 | 4.1 | 4.1 |
| TYPE CAT | ←PACAT→ | | | | |
| REACTOR TEMP, °C. | ←30→ | | | | |
| RESIDENCE TIME, hr | ←10.5→ | | | | |
| PRODUCT COMP, % | | | | | |
| AN | 12.6 | 10.3 | 12.4 | 16.8 | 12.0 |
| CDCB | 5.52 | 6.74 | 4.65 | 3.50 | 6.75 |
| TCB | 1.90 | 2.86 | 1.30 | 0.64 | 1.56 |
| MEGN | 0.34 | 0.40 | 0.33 | 0.28 | 0.38 |
| H.B. | 0.82 | 0.60 | 0.65 | 0.84 | 0.62 |
| SOLIDS | 0.06 | 0.02 | 0 | 0.001 | 0.02 |
| PRODUCT SELEC., % | | | | | |
| DCB | 85.9 | 90.4 | 86.0 | 78.7 | 89.1 |
| MEGN | 3.9 | 3.8 | 4.6 | 5.3 | 4.1 |
| H.B. | 9.5 | 5.6 | 9.4 | 16.0 | 6.6 |
| SOLIDS | 0.7 | 0.2 | 0 | <.1 | 0.2 |

TABLE 3
Effect of Formamide On DIMER Synthesis

| EXAMPLE | 16 | 17 | 18 | 19 | 20 | 21 | 22 | 23 | 24 |
|---|---|---|---|---|---|---|---|---|---|
| FEED COMP, % | | | | | | | | | |
| AN | 19.5 | 19.2 | 19.0 | 18.8 | 20.9 | 20.5 | 20.1 | 20.0 | 19.8 |
| IPA | 0 | 0 | 0 | 0 | 0 | 0 | 0 | 0 | 0 |
| FORMAMIDE | 7.2 | 7.9 | 9.2 | 10.1 | 1.0 | 3.1 | 4.1 | 5.1 | 6.0 |
| TOL | 69.3 | 68.9 | 67.8 | 67.1 | 64.0 | 72.3 | 71.8 | 71.0 | 70.2 |
| CAT | 4.1 | 4.0 | 4.0 | 4.1 | 4.1 | 4.1 | 4.1 | 4.0 | 4.0 |
| TYPE CAT | ←PACAT→ | | | | | | | | |
| REACTOR TEMP, °C. | ←30→ | | | | | | | | |

TABLE 3-continued

| | Effect of Formamide On DIMER Synthesis | | | | | | | | |
|---|---|---|---|---|---|---|---|---|---|
| EXAMPLE | 16 | 17 | 18 | 19 | 20 | 21 | 22 | 23 | 24 |
| RESIDENCE TIME, hr | 5.5 | 4.5 | 3.5 | 2.5 | 10.5 | 10.5 | 10.5 | 10.5 | 10.5 |
| PRODUCT COMP, % | | | | | | | | | |
| AN | 14.3 | 14.2 | 14.9 | 15.6 | 12.8 | 10.7 | 10.8 | 11.0 | 10.9 |
| IPA | | | | | | | | | |
| TOL | | | | | | | | | |
| CDCB | 3.25 | 2.64 | 2.07 | 1.55 | 5.47 | 6.46 | 6.24 | 6.11 | 6.10 |
| TDCB | 0.78 | 0.70 | 0.54 | 0.40 | 1.28 | 1.72 | 1.69 | 1.65 | 1.66 |
| MEGN | 0.16 | 0.11 | 0.10 | 0.06 | 0.31 | 0.33 | 0.32 | 0.31 | 0.30 |
| H.B. | 0.39 | 0.32 | 0.32 | 0.26 | 0.60 | 0.53 | 0.49 | 0.55 | 0.53 |
| SOLIDS | — | — | — | — | — | — | — | — | — |
| PROD. MEAS. | 4.58 | 3.71 | 3.03 | 2.27 | 7.66 | 9.04 | 8.74 | 8.62 | 8.59 |
| UNACCT. | 0.62 | 1.23 | 1.07 | 0.93 | 0.44 | 0.76 | 0.46 | 0.38 | 0.31 |
| PROD. SELEC., % | | | | | | | | | |
| DCB | 87.1 | 87.7 | 85.2 | 85.0 | 87.2 | 89.6 | 89.8 | 89.1 | 89.4 |
| MEGN | 3.5 | 2.9 | 3.3 | 2.6 | 4.0 | 3.6 | 3.6 | 3.6 | 3.5 |
| H.B. | 8.4 | 8.4 | 10.5 | 11.4 | 7.8 | 5.8 | 5.6 | 6.3 | 6.1 |
| SOLIDS | 1.0 | 1.0 | 1.0 | 1.0 | 1.0 | 1.0 | 1.0 | 1.0 | 1.0 |
| % AN CONV. | 25 | 23 | 19 | 14 | 38 | 46 | 45 | 44 | 44 |

Catalyst was added last and the reaction vial placed in an oven at the desired temperature for the specified time. Runs were terminated by quenching the reaction. The soluable organics were analyzed by gas chromatography. Solids were filtered, washed with methanol, dried and weighed.

EXAMPLE 25

A 250 ml round bottom flask with teflon sleeve and teflon plug stopcock was dried and purged with nitrogen. To the flask was charged
  74.7 g: Toluene
  18.1 g: Acrylonitrile
  32.2 g: Formamide
  2.1 g: Dicyanobutenes (DCB)
  4.0 g: Catalyst
which has been dried over molecular sieves.

The catalyst was isopropyl diphenylphosphinite (PACAT) The contents of the flask were mixed by shaking the flask and the flask was placed in an oven maintained at 30° C. After 3 hours the flask was removed, mixed by shaking, allowed to settle for 2 minutes, and a 1 ml sample of light phase was withdrawn, a 1 ml sample of heavy phase was withdrawn, 2 g of acrylonitrile were added to the flask, the contents were mixed by shaking, and the flask again placed in the 30° oven. The above procedure was repeated after 6 hours, 9 hours, and 12 hours, from time of initial mixing, with the exception that no acrylonitrile was added after 12 hours when the run was terminated. The flask contents at run termination were filtered using a 5 micron teflon pad. The cake was washed with methanol, dried overnight at 105° C., and weighed to determine the amount of solids formed. Both the light phase and heavy phase samples were quenched immediately after pulling to stop further reaction by adding to 6 mls of solution containing:
  0.7%: $H_2O_2$
  1.6%: $H_2O$
  4.0%: Valeronitrile
  2.0%: Azaleanitrile
  91.7%: Dimethyl Formamide

TABLE 4

| | Two Phase CANDID Synthesis with Formamide | | | | | | | | | | | |
|---|---|---|---|---|---|---|---|---|---|---|---|---|
| | CHARGE | | | | | | | | | | | |
| FEED COMP, % | | | | | | | | | | | | |
| AN | 13.8[1] | — | — | — | — | — | — | — | — | — | — | — |
| FORM | 24.6 | — | — | — | — | — | — | — | — | — | — | — |
| TOL | 57 | — | — | — | — | — | — | — | — | — | — | — |
| CDCB-1 | 1.1 | — | — | — | — | — | — | — | — | — | — | — |
| TDCB-1 | 0.5 | — | — | — | — | — | — | — | — | — | — | — |
| MEGN | 0 | — | — | — | — | — | — | — | — | — | — | — |
| PACAT | 3.1 | — | — | — | — | — | — | — | — | — | — | — |
| REACTOR TEMP, °C. | 30 | → | → | → | → | → | → | → | → | → | → | → | → |
| RESIDENCE TIME, hr | | 3 | 3 | 3[1] | 6[2] | 6 | 6[3] | 9[4] | 9 | 9[5] | 12[6] | 12 | 12 |
| PHASE | | U.L. | L.L. | Σ | U.L. | L.L. | Σ | U.L. | L.L. | Σ | U.L. | L.L. | Σ |
| wt % Phase | | 72.4 | 27.6 | 100 | 72.9 | 27.1 | 100 | 71.8 | 28.2 | 100 | 72.3 | 27.7 | 100 |
| PRODUCT COMP, % | | | | | | | | | | | | | |
| AN | | 12.7 | 8.0 | 11.4 | 14.3 | 8.1 | 12.6 | 14.5 | 8.1 | 12.7 | 14.5 | 8.1 | 12.7 |
| FORM | | 1.4 | 85 | 24.5 | 1.5 | 82 | 23.3 | 1.7 | 81 | 24.1 | 1.7 | 77 | 22.6 |
| TOL | | 77.4 | 3.7 | 57 | 75.5 | 4.0 | 56.4 | 76.7 | 4.4 | 55.8 | 74.9 | 4.7 | 55.2 |
| CDCB-1 | | 1.67 | 2.31 | 1.85 | 2.77 | 3.25 | 2.90 | 3.68 | 4.25 | 23.84 | 4.57 | 5.22 | 4.75 |
| TDCB-1 | | 0.51 | 0.82 | 0.60 | 0.74 | 1.09 | 0.83 | 0.95 | 1.43 | 1.09 | 1.17 | 1.74 | 1.33 |
| MEGN | | 0.034 | 0.01 | 0.027 | 0.08 | 0.03 | 0.067 | 0.13 | 0.05 | 0.11 | 0.17 | 0.08 | 0.14 |
| H.B. | | 0.38 | 0.32 | 0.36 | 0.49 | 0.69 | 0.54 | 0.41 | 0.77 | 0.51 | 0.39 | 1.13 | 0.59 |
| PSCAT, % AN | | 0.03 | 0.07 | 0.04 | 0.06 | 0.15 | 0.08 | 0.09 | 0.21 | 0.12 | 0.13 | 0.3 | 0.18 |
| (spent catalyst - AN content) | | | | | | | | | | | | | |
| SOLIDS | | — | — | 0.05 | — | — | 0.10 | — | — | 0.15 | — | — | 0.20 |

TABLE 4-continued
Two Phase CANDID Synthesis with Formamide
CHARGE

| PACAT | 4.0 | 0.02 | 2.9 | 4.1 | 0.02 | 3.0 | 3.8 | 0.02 | 2.7 | 3.3 | 0.03 | 2.4 |
|---|---|---|---|---|---|---|---|---|---|---|---|---|

[1]131.14 g = Total charge.
[2]2.062 g AN added following 3 hour samples.
[3]0.8746 g U.L. and 1.1304 g L.L. removed for analyses.
[4]2.022 g AN added following 6 hour samples.
[5]0.8632 g U.L. and 1.067 g L.L. removed for analyses.
[6]2.048 g AN added following 9 hour sample.

The samples were analyzed with a gas chromatograph to determine compositions and selectives. Results are shown in Table 4.

EXAMPLES 26-34

(showing the use of formamide as an extraction solvent where the extraction solvent is not the proton-donating solvent in the reaction)

In the following examples, the reactor effluents were simulated in the sense that they were formulated based upon typical reactor effluents in which isopropyl alcohol was used as the proton-donating solvent, as in the prior examples.

EXAMPLE 26

A mixture of simulated reactor effluent (less catalyst) was prepared as follows:
73.8%: Toluene
6.43%: IPA
9.7%: DCB
10%: AN
To 8.201 grams of this mixture was added 0.326 grams catalyst to form the simulated reactor effluent. To the simulated reactor effluent was added 11.463 grams formamide, and this was placed in a separatory funnel held at 0° C. for one hour with intermittent vigorous mixing. At the end of the period the two phases were separated and analyzed. The results of the analysis are shown at Table 5.

EXAMPLE 27

To 42.094 of the simulated reactor effluent less catalyst used in example 1 was added 1.710 grams PACAT and 5.825 grams of formamide. The procedure was otherwise the same as example 26.

EXAMPLE 28

11.41 grams formamide was added to 8.909 grams of a simulated reactor effluent consisting of:
24.65%: IPA
4.96%: AN
39.38%: Toluene
30.49%: DCB
0.52%: PACAT
The same extraction procedure was employed as in example 26.

EXAMPLE 29

11.43 grams formamide was added to 8.55 grams of a simulated reactor effluent consisting of:
14.92%: IPA
7.02%: AN
56.73%: Toluene
20.27%: DCB
1.07%: PACAT
The same extraction procedure was used as in example 26.

EXAMPLE 30

11.594 grams formamide was added to 8.812 grams of a simulated reactor effluent consisting of:
6.02%: IPA
10.01%: AN
69.55%: Toluene
10.43%: DCB
3.99%: PACAT
The same extraction procedure was employed as in example 26.

EXAMPLE 31

11.368 grams formamide was added to 8.670 grams of a simulated reactor effluent consisting of:
2.92%: IPA
11.95%: AN
72.83%: Toluene
7.30%: DCB
4.99%: PACAT
The same extraction procedure was employed as in example 26.

EXAMPLE 32

11.457 grams formamide was added to 8.925 grams of a simulated reactor effluent consisting of:
2.01%: IPA
11.94%: AN
76.92%: Toluene
4.12%: DCB
5.01%: PACAT
The same extraction procedure was employed as in example 26.

EXAMPLE 33

11.393 grams of formamide was added to 8.827 grams of a simulated reactor effluent consisting of:
1.07%: IPA
12.80%: AN
79.14%: Toluene
2.08%: DCB
4.91%: PACAT
The same extraction procedure was used as in example 26.

EXAMPLE 34

11.521 grams of formamide was added to 8.805 grams of a simulated reactor effluent consisting of:
0.71%: IPA
13.44%: AN
79.76%: Toluene
1.06%: DCB
5.03%: PACAT
The same extraction procedure was used as in example 26.

TABLE 5

| | Formamide Extraction | | | | | | | | |
|---|---|---|---|---|---|---|---|---|---|
| | Example | | | | | | | | |
| | 26 | 27 | 28 | 29 | 30 | 31 | 32 | 33 | 34 |
| g, Upper Layer | 6.527 | 41.959 | 2.174 | 4.671 | 6.304 | 6.848 | 7.398 | 7.503 | 7.537 |
| Composition, wt % | | | | | | | | | |
| IPA | 0.72 | 4.71 | 4.83 | 2.61 | 0.97 | 0.49 | 0.35 | 0.20 | 0.14 |
| AN | 5.04 | 8.95 | 2.21 | 3.23 | 4.75 | 5.98 | 6.16 | 6.78 | 7.18 |
| Toluene | 80.84 | 66.82 | 77.48 | 79.73 | 78.66 | 77.44 | 75.92 | 77.31 | 77.44 |
| DCB | 2.40 | 8.07 | 7.71 | 4.92 | 2.47 | 1.79 | 1.01 | 0.54 | 0.31 |
| Cat. Active | 5.25 | 3.88 | 0.66 | 1.63 | 4.72 | 6.23 | 6.18 | 5.87 | 6.00 |
| Cat. Spent | 0.09 | 0.35 | 0.12 | 0.11 | 0.23 | 0.23 | 0.18 | 0.16 | 0.21 |
| Form. (by diff) | 5.66 | 7.22 | 6.99 | 7.77 | 8.20 | 7.84 | 10.20 | 9.14 | 8.72 |
| g, Lower Layer | 13.162 | 7.443 | 17.962 | 15.431 | 13.836 | 12.915 | 12.697 | 12.491 | 12.526 |
| Composition, wt % | | | | | | | | | |
| IPA | 2.91 | 9.94 | 13.31 | 8.67 | 3.79 | 1.86 | 1.30 | 0.72 | 0.48 |
| AN | 2.67 | 5.25 | 1.83 | 2.52 | 3.47 | 4.17 | 4.25 | 4.56 | 4.79 |
| Toluene | 2.75 | 6.51 | 9.06 | 6.19 | 4.31 | 3.69 | 3.47 | 3.25 | 3.21 |
| DCB | 4.75 | 9.96 | 13.19 | 9.21 | 4.97 | 3.51 | 1.98 | 1.11 | 0.55 |
| Cat. Active | 0.01 | 0.04 | 0.02 | 0.02 | 0.01 | 0.01 | 0.03 | 0.02 | 0.01 |
| Cat. Spent | 0.06 | 0.72 | 0.18 | 0.13 | 0.48 | 0.030 | 0.22 | 0.23 | 0.19 |
| Form. (by diff) | 86.85 | 67.58 | 62.41 | 73.26 | 82.97 | 86.46 | 88.75 | 90.11 | 90.77 |

We claim:

1. In a process for the production of 1,4-dicyano-1-butene from acrylonitrile where the acrylonitrile is catalytically dimerized in the presence of an organic phosphorus (III) catalyst, selected from the group consisting of phosphinites and phosphonites, an inert hydrocarbon reaction slovent and a non-interfering proton-donating solvent; and the dimerized product is thereafter separated from the catlyst by extraction, the improvement characterized in that in the extraction the dimerized product is dissolved in an extraction solvent consisting essentially of an amide of the empirical formula

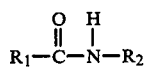

where $R_1$ and $R_2$ individually have 0-6 carbon atoms and are individually selected from the group consisting of hydrogen, alkyl, cycloalkyl and aryl, and is removed from the catalyst by phase separation.

2. The process improvement of claim 1 wherein the amide is formamide.

3. In a process for the production of 1,4-dicyano-1-butene from acrylonitrile where the acrylonitrile is catalytically dimerized in the presence of a homogeneous organic phosphorus (III) catalyst, an aromatic hydrocarbon reaction solvent and a proton donating solvent; and the dimerized product is thereafter separated from the catalyst by extraction, the improvement charactered in that in the extraction the dimerized product is dissolved in an extraction solvent and removed from the catalyst by phase separation, the extraction solvent and the proton-donating solvent comprising essentially of an amide of the empirical formula

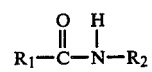

wherein $R_1$ and $R_2$ individually have 0-6 carbon atoms and are individually selected from the group consisting of hydrogen, alkyl, cycloalkyl and aryl.

4. The process improvement of claim 3 wherein both the proton donating solvent and extraction solvent are formamide.

* * * * *